United States Patent [19]

Smith

[11] Patent Number: 5,837,502
[45] Date of Patent: Nov. 17, 1998

[54] HELICOBACTER PYLORI HAEMAGGLUTININ PROTEASE PROTEIN, NUCLEIC ACID ENCODING THEREFOR AND ANTIBODIES SPECIFIC THERETO

[75] Inventor: Andrew William Smith, Kent, Great Britain

[73] Assignee: Reckitt & Colman Products Limited, London, United Kingdom

[21] Appl. No.: 578,516

[22] PCT Filed: Jun. 29, 1994

[86] PCT No.: PCT/GB94/01406

§ 371 Date: Sep. 16, 1996

§ 102(e) Date: Sep. 16, 1996

[87] PCT Pub. No.: WO95/01445

PCT Pub. Date: Jan. 12, 1995

[30] Foreign Application Priority Data

Jun. 30, 1993 [GB] United Kingdom .................. 9313437

[51] Int. Cl.$^6$ ........................... C12P 19/34; C12N 15/00; C07K 13/00; C07K 15/28
[52] U.S. Cl. ........................ 435/91.2; 435/320.1; 435/6; 435/252.3; 435/325; 530/350; 530/388.1; 536/24.32; 536/22.1; 536/23.7
[58] Field of Search .................................. 536/22.1, 23.7; 435/320.1, 91.2, 6, 252.3, 325; 530/350

[56] References Cited

U.S. PATENT DOCUMENTS

| | | | |
|---|---|---|---|
| 4,965,188 | 10/1990 | Mullis et al. | 435/6 |
| 5,234,910 | 8/1993 | Cave | 514/21 |
| 5,403,924 | 4/1995 | Cover et al. | 536/23.1 |

FOREIGN PATENT DOCUMENTS

| | | |
|---|---|---|
| 0 329 570 | 8/1989 | European Pat. Off. . |
| 0 350 205 | 1/1990 | European Pat. Off. . |
| 0 367 644 | 5/1990 | European Pat. Off. . |
| WO 89/08843 | 9/1989 | WIPO . |
| WO 89/09497 | 10/1989 | WIPO . |
| WO 91/09049 | 6/1991 | WIPO . |

OTHER PUBLICATIONS

Ho et al. Direct Polymerase Chain Reaction Test for Detection of *Helicobacter pylori* in Humans and Animals, J. of Clinical Microbiology, vol. 29(11), pp. 2543–2549, 1991.

Xing et al. Detection in an Enzyme Immunoassay of an Immune Response to a Recombinant Fragment of the 128 Kilodalton Protein (CagA) of *Helicobacter pylori*. vol. 12(10), pp. 739–745, 1993.

Smith et al. The Human Gastric Pathogen *Helicobacter Pylori* has a Gene Encoding an Enzyme First Classified as a Mucinase in *Vibrio Cholerae*, Molecular Microbiology, vol. 13(1), pp. 153–160, 1994.

"Cloning and Nucleotide Sequence of the *Vibrio cholerae* Hemagglutinin/Protease (HA/Protease) Gene and Construction of an HA/Proteases–Negative Strain", *Journal of Bacteriology*, by C.C. Häse and R.A. Finkelstein, vol. 173, No. 11, Jun. 1991, pp. 331–3317.

"Molecular Characterization and Nucleotide Sequence of the *Pseudomanas aeruginosa* Elastase Structural Gene", *Journal of Bacteriology*, by R.A. Bever and B.H. Iglewski, vol. 170, No. 9, Sep. 1988, pp. 4309–4314.

"Purification and Characterization of the Soluble Hemagglutinin (*Cholera Lectin*) Produced by *Vibrio cholerae*", *Infection and Immunity*, by R.A. Finkelstein and L.F. Hanne, vol. 36, No. 3, Jun. 1982, pp. 1199–1208.

*Vibrio cholerae* Hemagglutinin/Protease, Colonial Variation, Virulence, and Detachment, *Infection and Immunity*, by R.A. Finkelstein, M. Boesman–Finkelstein, Y. Chang and C.C. Häse, vol. 60, No. 2, Feb. 1992, pp. 472–478.

The human gastric pathogen *Helicobacter pylori* has a gene encoding an enzyme first classified as a mucinase in *Vibrio cholerae*, *Molecular Microbiology*, by A.W. Smith, B. Chahal and G.L. French, vol. 13, No. 1, 1994, pp. 153–160.

Comparison of urease gene primer sequences for PCR––based amplification assays in identifying the gastric pathogen *Helicobacter pylori*, *Molecular and Cellular Probes*, by C.R. Lopez, R.J. Owen, N. Banatvala, Y. Abdi, J.M. Hardie, G.R. Davies and R. Feldman, vol. 7, No. 6, Dec. 1993, pp. 439–446.

"*Campylobacter pyloridis*–associated gastritis" (Review) *Journal of Infection*, by Cliodna A.M. McNulty, vol. 13, No. 1, 1986, pp. 107–113.

"*Campylobacter pyloridis*, gastritis, and peptic ulceration" (Review article) *J. J. Clin Pathol*, vol. 39, 1986, pp. 353–365.

"An international association between *Helicobacter pylori* infection and gastric cancer", *The Lancet*, by The Eurogast Study Group, vol. 341, No. 8857, May 29, 1993, pp. 1359–1362.

"Zinc Coordination, Function, and Structure of Zinc Enzymes and Other Proteins", *Biochemistry*, by B.L. Valee and D.S. Auld, vol. 29, No. 24, Jun. 19, 1990, pp. 5647–5649.

"Zinc: Lewis acid catalysis and regulation", Chapter 11 of *The Biological Chemistry of the Elements*, by Frausto da Silva, J.J.R. and Williams R.J.P., 1993, pp. 299–318.

Primary Examiner—Kenneth R. Horlick
Assistant Examiner—Joyce Tung
Attorney, Agent, or Firm—Wolf, Greenfield & Sacks, P.C.

[57] ABSTRACT

*Helicobacter pylori* (*H.pylori*) haemagglutinin/protease protein, nucleic acids encoding therefor and antibodies specific thereto are described and, in particular, to their use in the identification of *H.pylori* and in the diagnosis of *H.pylori* infection. Also described are kits for the identification and diagnosis of *H.pylori* infection.

18 Claims, 2 Drawing Sheets

FIG. 1.

```
EcoRI                                                       60
GAATTCAGGCCTCGTTTACCGAGATATGTCCGGTGGTATTAACGAAGCATTCTCGGATATC
  AsnSerGlyLeuValTyrArgAspMetSerGlyGlyIleAsnGluAlaPheSerAspIle
                                    SalI                   120
GCAGGGGAAGCGGCAGAGTACTTTATGCGTGGCAATGTCGACTGGATTGTCGGCGCGGAT
AlaGlyGluAlaAlaGluTyrPheMetArgGlyAsnValAspTrpIleValGlyAlaAsp
                                                           180
ATTTTTAAATCCTCCGGTGGTCTACGTTATTTCGATCAGCCGTCACGTGATGGCCGCTCG
IlePheLysSerSerGlyGlyLeuArgTyrPheAspGlnProSerArgAspGlyArgSer
                                ΔH                         240
ATAGATCATGCTTCACAGTATTACAGCGGTATTGATGTTCATTCGAGTGGCGTGTTTAAC
IleAspHisAlaSerGlnTyrTyrSerGlyIleAspValHisSerSerGlyValPheAsn
                                                           300
CGCGCGTTTTACCTACTCGCCAATAAATCGGGTTGGAACGTACGTAAAGGTTTTGAAGTG
ArgAlaPheTyrLeuLeuAlaAsnLysSerGlyTrpAsnValArgLysGlyPheGluVal
                                                           360
TTTGCCGTGGCTAACCAGTTGTACTGGACACCGAACAGCACGTTTGATCAAGGTGGCTGT
PheAlaValAlaAsnGlnLeuTyrTrpThrProAsnSerThrPheAspGlnGlyGlyCys
                                                           420
GGGGTAGTGAAAGCGGCGCAGGATCTCAACTACAACACCGCAGACGTTGTGGCAGCCTTT
GlyValValLysAlaAlaGlnAspLeuAsnTyrAsnThrAlaAspValValAlaAlaPhe
                                                           480
AATACCGTGGGTGTCAATGCTTCTTGTGGCACCACGCCACCACCTGTCGGCAAAGTGCTT
AsnThrValGlyValAsnAlaSerCysGlyThrThrProProProValGlyLysValLeu
                                                           540
GAGAAAGGTAAACCGATCACAGGACTGAGCGGCTCACGTGGAGGAGAAGATTTCTATACC
GluLysGlyLysProIleThrGlyLeuSerGlySerArgGlyGlyGluAspPheTyrThr
                                                           600
TTTACGGTGACCAATTCAGGCAGTGTTGTTGTGTCCATCAGTGGTGGAACGGGCGATGCG
PheThrValThrAsnSerGlySerValValValSerIleSerGlyGlyThrGlyAspAla
                                                           660
GATCTGTATGTCAAAGCGGGCAGCAAACCCACCACCTCTTCTTGGGATTGTCGTCCATAC
AspLeuTyrValLysAlaGlySerLysProThrThrSerSerTrpAspCysArgProTyr
                                                           720
CGTTCAGGCAATGCCGAGCAGTGTTCCATCTCTGCGGTCGTGGGTACGACATACCATGTC
ArgSerGlyAsnAlaGluGlnCysPheIleSerAlaValValGlyThrThrTyrHisVal
                                                           780
ATGTTACGCGGTTACAGTAACTATTCTGGTGTGACGTTACGCTTGGACTAACTTCCTTGC
MetLeuArgGlyTyrSerAsnTyrSerGlyValThrLeuArgLeuAsp***
                                                           840
CACCTACCTGCAACGCCCTCAGCAAAGTCTGAGGGCGTTGTTTTGAAGGGCAGTTTCTA
                                                           900
GGATGTATCAACTATTTGAGTTGGCTGACCGCCGAAGAAACATTTTCTGCACCTTGGTAA
                                                           960
ATCTGTTCCATGATGGTTGACACTTCCACAATGCGGCCATTGGTTTCATTGGCAATGTGA
                                                          1020
GAGACTTGAGAAATAGAGCTGGTTACCGCTTCAGTTAAGGAGAGGTTTTTATTCACCACT
                                                          1080
TGATTGATCTCTTCTGTGGCTTTTGAGGTGCGAGAACGCAGTTGACCGACTTCATCGGCA
                                                          1140
AACCACCGCAAAACCGCGTCCTTGATCAACCGCTGCGACGCTCTATCGCTGCATTAATGC
                                                          1200
GGAGCAGATGGTTTGGTCAGCGATACACTGATGGTTTTGACAATTTCAGAGACATCTTTC
                                                          1260
GAGAGAACCACGAGCTGCTCAATCTGTTGTAGTGATTGTTCGATATTGCCCACCATTTTT
                                                          1320
TCTGCTAACGACTGAATCTTGCAGTACATGTTCCGCCTTGTGCTACTTGCGAGGTTCTAC
                                                    PstI1380
TGAGGTGCTATAGGCGATATTGGCAGCGTCTGTTACTTGCTGTTCACGTAATACCTCTGC
                                                          1440
AGTGATGTCTGAGGCGAACTTGACAATTTTATATACCTTATTGTTTTGATCTTTGACCGG
                     1460
ACTGTAGGAGGCTTGGATCC
             BamHI
```

FIG. 2.

SEQUENCE LISTING ( 1 ) GENERAL INFORMATION:

( i i i ) NUMBER OF SEQUENCES: 6

( 2 ) INFORMATION FOR SEQ ID NO: 1:

( i ) SEQUENCE CHARACTERISTICS:
        ( A ) LENGTH: 1461 base pairs
        ( B ) TYPE: nucleic acid
        ( C ) STRANDEDNESS: double
        ( D ) TOPOLOGY: linear     ( i i ) MOLECULE TYPE: DNA (genomic)

( i i i ) HYPOTHETICAL: NO

( i i i ) ANTI-SENSE: NO

( v i ) ORIGINAL SOURCE:
        ( A ) ORGANISM: HELICOBACTER PYLORI
        ( B ) STRAIN: H.PYLORI NCTC 11638

( x i ) SEQUENCE DESCRIPTION: SEQ ID NO: 1:

```
GAATTCAGGC   CTCGTTTACC   GAGATATGTC   CGGTGGTATT   AACGAAGCAT   TCTCGGATAT        60
CGCAGGGGAA   GCGGCAGAGT   ACTTTATGCG   TGGCAATGTC   GACTGGATTG   TCGGCGCGGA       120
TATTTTTAAA   TCCTCCGGTG   GTCTACGTTA   TTTCGATCAG   CCGTCACGTG   ATGGCCGCTC       180
GATAGATCAT   GCTTCACAGT   ATTACAGCGG   TATTGATGTT   CATTCGAGTG   GCGTGTTTAA       240
CCGCGCGTTT   TACCTACTCG   CCAATAAATC   GGGTTGGAAC   GTACGTAAAG   GTTTTGAAGT       300
GTTTGCCGTG   GCTAACCAGT   TGTACTGGAC   ACCGAACAGC   ACGTTTGATC   AAGGTGGCTG       360
TGGGGTAGTG   AAAGCGGCGC   AGGATCTCAA   CTACAACACC   GCAGACGTTG   TGGCAGCCTT       420
TAATACCGTG   GGTGTCAATG   CTTCTTGTGG   CACCACGCCA   CCACCTGTCG   GCAAAGTGCT       480
```

-continued

```
TGAGAAAGGT AAACCGATCA CAGGACTGAG CGGCTCACGT GGAGGAGAAG ATTTCTATAC      540
CTTTACGGTG ACCAATTCAG GCAGTGTTGT TGTGTCCATC AGTGGTGGAA CGGGCGATGC      600
GGATCTGTAT GTCAAAGCGG GCAGCAAACC CACCACCTCT TCTTGGGATT GTCGTCCATA      660
CCGTTCAGGC AATGCCGAGC AGTGTTCCAT CTCTGCGGTC GTGGGTACGA CATACCATGT      720
CATGTTACGC GGTTACAGTA ACTATTCTGG TGTGACGTTA CGCTTGGACT AACTTCCTTG      780
CCACCTACCT GCAACGCCCT CAGCAAAGTC TGAGGGCGTT GTTTTGAAG GGCAGTTTCT       840
AGGATGTATC AACTATTTGA GTTGGCTGAC CGCCGAAGAA ACATTTCTG CACCTTGGTA       900
AATCTGTTCC ATGATGGTTG ACACTTCCAC AATGCGGCCA TTGGTTTCAT TGGCAATGTG      960
AGAGACTTGA GAAATAGAGC TGGTTACCGC TTCAGTTAAG GAGAGGTTTT TATTCACCAC     1020
TTGATTGATC TCTTCTGTGG CTTTTGAGGT GCGAGAACGC AGTTGACCGA CTTCATCGGC     1080
AAACCACCGC AAAACCGCGT CCTTGATCAA CCGCTGCGAC GCTCTATCGC TGCATTAATG     1140
CGGAGCAGAT GGTTTGGTCA GCGATACACT GATGGTTTTG ACAATTCAG AGACATCTTT      1200
CGAGAGAACC ACGAGCTGCT CAATCTGTTG TAGTGATTGT TCGATATTGC CCACCATTTT     1260
TTCTGCTAAC GACTGAATCT TGCAGTACAT GTTCCGCCTT GTGCTACTTG CGAGGTTCTA     1320
CTGAGGTGCT ATAGGCGATA TTGGCAGCGT CTGTTACTTG CTGTTCACGT AATACCTCTG     1380
CAGTGATGTC TGAGGCGAAC TTGACAATTT TATATACCTT ATTGTTTTGA TCTTTGACCG     1440
GACTGTAGGA GGCTTGGATC C                                               1461
```

( 2 ) INFORMATION FOR SEQ ID NO: 2:

( i ) SEQUENCE CHARACTERISTICS:
        ( A ) LENGTH: 18 bases
        ( B ) TYPE: nucleic acid
        ( C ) STRANDEDNESS: single
        ( D ) TOPOLOGY: linear     ( i i ) MOLECULE TYPE: synthetic     ( i i i ) HYPOTHETICAL: NO     ( i v ) ANTI-SENSE: NO     ( v ) ORIGINAL SOURCE:
        ( A ) ORGANISM: HELICOBACTER PYLORI
        ( B ) STRAIN: H.PYLORI NCTC 11638

( x i ) SEQUENCE DESCRIPTION: SEQ ID NO: 2:

```
GCACAGGCAA CAGGAACC                                                     18
```

( 2 ) INFORMATION FOR SEQ ID NO: 3:

( i ) SEQUENCE CHARACTERISTICS:
        ( A ) LENGTH: 19 bases
        ( B ) TYPE: nucleic acid
        ( C ) STRANDEDNESS: single
        ( D ) TOPOLOGY: linear     ( i i ) MOLECULE TYPE: synthetic     ( i i i ) HYPOTHETICAL: NO     ( i v ) ANTI-SENSE: YES     ( v ) ORIGINAL SOURCE:
        ( A ) ORGANISM: HELICOBACTER PYLORI
        ( B ) STRAIN: H.PYLORI NCTC 11638

( x i ) SEQUENCE DESCRIPTION: SEQ ID NO: 3:

```
AACGAGGCCT GAATTCTGC                                                    19
```

( 2 ) INFORMATION FOR SEQ ID NO: 4:

( i ) SEQUENCE CHARACTERISTICS:
        ( A ) LENGTH: 20 bases
        ( B ) TYPE: nucleic acid
        ( C ) STRANDEDNESS: single
        ( D ) TOPOLOGY: linear     ( i i ) MOLECULE TYPE: synthetic     ( i i i ) HYPOTHETICAL: NO     ( i v ) ANTI-SENSE: YES     ( v ) ORIGINAL SOURCE:
        ( A ) ORGANISM: HELICOBACTER PYLORI
        ( B ) STRAIN: H.PYLORI NCTC 11638

( x i ) SEQUENCE DESCRIPTION: SEQ ID NO: 4:

ATAACGTAGA CCACCGGAGG                    20

( 2 ) INFORMATION FOR SEQ ID NO: 5:

( i ) SEQUENCE CHARACTERISTICS:
        ( A ) LENGTH: 20 bases
        ( B ) TYPE: nucleic acid
        ( C ) STRANDEDNESS: single
        ( D ) TOPOLOGY: linear     ( i i ) MOLECULE TYPE: synthetic     ( i i i ) HYPOTHETICAL: NO     ( i v ) ANTI-SENSE: NO     ( v ) ORIGINAL SOURCE:
        ( A ) ORGANISM: HELICOBACTER PYLORI
        ( B ) STRAIN: H.PYLORI NCTC 11638

( x i ) SEQUENCE DESCRIPTION: SEQ ID NO: 5:

TCCGGTGGTA TTAACGAAGC                    20

( 2 ) INFORMATION FOR SEQ ID NO: 6:

( i ) SEQUENCE CHARACTERISTICS:
        ( A ) LENGTH: 256 amino acids
        ( B ) TYPE: amino acid
        ( C ) STRANDEDNESS: single
        ( D ) TOPOLOGY: unknown     ( i i ) MOLECULE TYPE: protein     ( i i i ) HYPOTHETICAL: NO     ( v ) FRAGMENT TYPE: internal     ( v i ) ORIGINAL SOURCE:
        ( A ) ORGANISM: HELICOBACTER PYLORI
        ( B ) STRAIN: H.PYLORI NCTC 11638

( x i ) SEQUENCE DESCRIPTION: SEQ ID NO: 6:

```
Asn  Ser  Gly  Leu  Val  Tyr  Arg  Asp  Met  Ser  Gly  Gly  Ile  Asn  Glu  Ala
 1              5                        10                       15

Phe  Ser  Asp  Ile  Ala  Gly  Glu  Ala  Ala  Glu  Tyr  Phe  Met  Arg  Gly  Asn
               20                       25                       30

Val  Asp  Trp  Ile  Val  Gly  Ala  Asp  Ile  Phe  Lys  Ser  Ser  Gly  Gly  Leu
          35                       40                       45

Arg  Tyr  Phe  Asp  Gln  Pro  Ser  Arg  Asp  Gly  Arg  Ser  Ile  Asp  His  Ala
     50                       55                       60
```

```
Ser  Gln  Tyr  Tyr  Ser  Gly  Ile  Asp  Val  His  Ser  Ser  Gly  Val  Phe  Asn
 65                        70                      75                         80

Arg  Ala  Phe  Tyr  Leu  Leu  Ala  Asn  Lys  Ser  Gly  Trp  Asn  Val  Arg  Lys
                     85                        90                         95

Gly  Phe  Glu  Val  Phe  Ala  Val  Ala  Asn  Gln  Leu  Tyr  Trp  Thr  Pro  Asn
               100                      105                        110

Ser  Thr  Phe  Asp  Gln  Gly  Gly  Cys  Gly  Val  Val  Lys  Ala  Ala  Gln  Asp
          115                      120                        125

Leu  Asn  Tyr  Asn  Thr  Ala  Asp  Val  Val  Ala  Ala  Phe  Asn  Thr  Val  Gly
     130                      135                         140

Val  Asn  Ala  Ser  Cys  Gly  Thr  Thr  Pro  Pro  Pro  Val  Gly  Lys  Val  Leu
145                       150                      155                        160

Glu  Lys  Gly  Lys  Pro  Ile  Thr  Gly  Leu  Ser  Gly  Ser  Arg  Gly  Gly  Glu
                    165                      170                         175

Asp  Phe  Tyr  Thr  Phe  Thr  Val  Thr  Asn  Ser  Gly  Ser  Val  Val  Val  Ser
               180                      185                         190

Ile  Ser  Gly  Gly  Thr  Gly  Asp  Ala  Asp  Leu  Tyr  Val  Lys  Ala  Gly  Ser
          195                      200                         205

Lys  Pro  Thr  Thr  Ser  Ser  Trp  Asp  Cys  Arg  Pro  Tyr  Arg  Ser  Gly  Asn
     210                      215                        220

Ala  Glu  Gln  Cys  Phe  Ile  Ser  Ala  Val  Val  Gly  Thr  Thr  Tyr  His  Val
225                       230                      235                         240

Met  Leu  Arg  Gly  Tyr  Ser  Asn  Tyr  Ser  Gly  Val  Thr  Leu  Arg  Leu  Asp
                    245                      250                         255
```

HELICOBACTER PYLORI HAEMAGGLUTININ PROTEASE PROTEIN, NUCLEIC ACID ENCODING THEREFOR AND ANTIBODIES SPECIFIC THERETO

The present invention relates to *Helicobacter pylori* (*H.pylori*) haemagglutinin/protease protein, nucleic acids encoding therefor and antibodies specific thereto and, in particular, to their use in the identification of *H.pylori* and in the diagnosis of *H.pylori* infection.

*H.pylori* (formerly *Campylobacter pyloridis* or *C.pylori*) is a spiral-shaped Gram negative microorganism which appears to live beneath the mucus layer of the stomach. Since its first isolation in 1982 *H.pylori* has been associated with gastric and duodenal ulcer disease and gastric cancer. *H.pylori* has been described as the most chronic infectious agent of man. Reviews on the state of the art include those by C. A. M. McNulty in *J. Infection,* 1986, 13, 107–113, C. S. Goodwin et al. in *J. Clin. Pathol.,* 1986, 39, 353–365 and the Eurogast Study Group, *Lancet,* 1993, 341, 1359–1362.

The number of genes that encode proteins that are involved in the ability of *H.pylori* to cause disease is unknown and virulence determinants of *H.pylori* have so far not been identified. A number of determinants possessed by this organism have been proposed as possible pathogenic factors. For example, multiple flagella allow the microorganism to move rapidly by a corkscrew-like motion through highly viscous fluids such as the mucus layer of the gut which normally poses a barrier to bacteria en route to the gut epithelium. Also, the ability of *H.pylori* to produce mucinase digesting enzymes allows the organism to spread in the stomach. Microscopic studies of gastric biopsies from patients with *H.pylori* infection have shown the *H.pylori* organisms at specific sites on the gastric epithelial cells. Biochemical studies have reported the identification of haemagglutinins that allow *H.pylori* to adhere to these sites.

Extracellular metalloprotease enzymes are common microbial pathogenicity factors in bacteria causing disease in mammals. Zinc metalloprotease enzymes are known to have rapid substrate turnover and broad substrate profiles. Reviews on the state of the art are by Frausto da Silva J. J. R and Williams R. J. P in, The Biological Chemistry of the Elements, 1993, Clarendon Press, Oxford, Chapter 11, and Vallee, B. L. and Auld D. S., *Biochemistry,* 29, 5647–5659.

The zinc metalloprotease enzyme of *Pseudomonas aeruginosa* (also known as the elastase enzyme) has been shown to be important in the lung tissue-destructive processes caused by this organism in cystic fibrosis patients, (Bever R. A. and Iglewski B. H., *J.Bacteriol.,* 1988, 170, 4309–4314). Similarly, the zinc metalloprotease enzyme of *Vibrio cholerae* (*V.cholerae*) (also known as the mucinase enzyme or haemagglutinin/protease (HAP) enzyme) has been shown to be important in the attachment and detachment of these organisms during the disease cholera. References on the state of the art include: Hase C. C. and Finkelstein R. A., *J. Bacteriol.,* 1991, 173, 3311–3317; and Finkelstein R. A. et al., *Infect.Immunol.* 1992, 60 472–478.

We have now surprisingly found that a virulance gene almost identical to the *V.cholerae hap* gene, which we have termed the *H.pylori hap* gene, is present in the *H.pylori* genome. The detection of the *H.pylori hap* nucleic acid sequence by polymerase chain reaction (PCR) or other hybridization methods, the detection of *H.pylori* HAP protein epitopes by antibody detection methods, or the detection of antibodies to the *H.pylori* HAP protein by, for example ELISA, have utility in the diagnosis of *H.pylori* mediated gastroduodenal disorders in mammals.

Prior art in the diagnosis of *H.pylori* mediated gastric diseases include *Campylobacter* DNA probes capable of hybridizing *H.pylori* RNA (EP-A-0350205). *H.pylori* oligonucleotides specific for the *H.pylori* urease gene sequences are disclosed in WO 91/09049. Serological detection and diagnosis of *H.pylori* infection by serological immunoassays and detection of *H.pylori* antigens and antigenic fragments are disclosed in WO 89/08843, WO 89/09497 and EP-A-0329570.

It would be highly desirable to have a reliable means of detecting *H.pylori* DNA, RNA or antibodies directed against specific *H.pylori* proteins or *H.pylori* proteins themselves in clinical samples from a patient (for example in the gastric mucosa, saliva, faecal samples plasma or serum), as means of early diagnosis of gastritis, gastric or peptic ulcerations, or of gastric cancer.

Accordingly, the present invention provides a nucleic acid sequence encoding the *H.pylori* HAP protein or a fragment thereof comprising all or part of the nucleic acid sequence of FIG. 1 known as Sequence No. 1.

The *H.pylori hap* gene of the present invention has been sequenced, giving rise to the possibility of constructing selected oligonucleotide or protein epitope sequences specific to *H.pylori*. The sequenced *H.pylori hap* gene has been found to be over 99% similar to the *V.cholerae hap* gene in the coding region. The nucleotide sequence of the cloned 1.5 kb *H.pylori hap* gene fragment showing the 1 kb of coding sequence and about 500 bp of 3' flanking sequence is shown in FIG. 1.

Preferably the nucleic acid sequence encodes at least one antigenic determinant of *H.pylori* HAP protein. Preferably the nucleic acid sequence comprises the sequences of bases numbered from 1 to 936 of FIG. 1. Also provided by the present invention is a nucleic acid sequence which is complementary to the *H.pylori hap* nucleic acid sequence as defined above. The nucleic acid sequence may comprise genomic DNA, complementary DNA (cDNA), synthetic DNA or recombinant DNA or RNA.

The nucleic acid sequence may comprise an oligonucleotide of from 15 to 50 nucleotides preferably from 18 to 50 nucleotides which has specific binding affinity for a portion of the nucleic acid sequence as shown in FIG. 1, or a nucleic acid sequence complementary thereto. The oligonucleotide may also be from 15 to 30 nucleotides, preferably from 15 to 25 nucleotides. Preferably the oligonucleotide comprises a sequence of at least 15 or more nucleotides and includes the nucleotides numbered 16 to 18 (inclusive), 220 to 222 (inclusive) or 43 to 45 (inclusive) as shown in FIG. 1.

Preferably the oligonucleotides are any of the following sequences:

5'- GCACAGGCAACAGGAACC-3' known as Sequence No. 2; or

5'- AACGAGGCCTGAATTCTGC-3' known as Sequence No. 3; or

5'- ATAACGTAGACCACCGGAGG-3' known as Sequence No. 5; or

5'- TCCGGTGGTATTAACGAAGC-3'.

The oligonucleotides may comprise DNA or RNA sequences.

The oligonucleotides within the scope of the present invention include both single- and double-stranded versions, it being understood that in any hybridization procedures such double stranded probes will require denaturing to provide the probes in single-stranded form.

The present invention further provides vectors which comprise any nucleic acid sequence as hereinbefore defined. The present invention specifically contemplates the provision of any vector system known in the art including cloning vectors such as pUC18 and pUC19 as well as expression vectors such as pASK60-Strep. Further provided by the present invention is a host cell transformed with one or more such vectors. The present invention also provides a process for the production of DNA sequences as hereinbefore defined comprising culturing a host cell which has been transformed with one or more vectors comprising the DNA sequence and isolating the DNA sequence therefrom. Such a process is carried out according to conditions and procedures well known in the art.

Further provided by the present invention is *H.pylori* HAP protein or a fragment thereof comprising all or a part of the amino acid sequence of FIG. 1 known as Sequence No. 6. Preferably the fragment of the HAP protein is an antigenic determinant of *H.pylori* HAP protein. Preferably the fragment of the HAP protein is encoded by the sequence of bases numbered from 1 to 936 of FIG. 1.

The *H.pylori* protein or fragment thereof within the scope by this invention include the *H.pylori* HAP protein itself, being purified from *H.pylori* or being produced as a recombinant protein in, for example *Escherichia coli* or *Bacillus subtilis,* it being understood that the subsequent diagnostic procedures such as the detection of the *H.pylori* protein in the gastric mucosa or other secretions or products of the gastrointestinal tract are within the scope of this invention.

The present invention also provides a process for the production of *H.pylori* HAP protein or a fragment thereof as hereinbefore described comprising culturing a host cell transformed with an expression vector as hereinbefore defined and isolating the protein or protein fragment produced therefrom.

It will be understood that in accordance with the present invention a defined nucleic acid sequence includes not only the identical nucleic acid sequence but also any minor base variations from the natural nucleic acid sequence including, in particular, substitutions in bases which result in a synonym codon (a different codon specifying the same amino acid). Furthermore a defined protein, polypeptide or amino acid sequence includes not only the identical amino acid sequence but also minor amino acid variations from the natural amino acid sequence including, in particular, conservative amino acid replacements (a replacement by an amino acid that is related in its side chains). Also included are amino acid sequences which vary from the natural amino acid but result in a polypeptide which is immunologically identical with the polypeptide encoded by the naturally occurring sequence. This includes a correspondingly altered encoding nucleic acid sequence.

The present invention also provides polyclonal and monoclonal antibodies which recognize an antigenic determinant of *H.pylori* HAP protein or a fragment thereof. The *H.pylori* specific antibodies covered by this invention include both polyclonal or monoclonal antibodies directed against the *H.pylori* HAP protein or a fragment thereof, it being understood that the subsequent diagnostic procedures such as the detection of antibodies against *H.pylori* in the gastric mucosa or other secretions or products of the gastrointestinal tract are within the scope of this invention.

The polyclonal and monoclonal antibodies are produced by standard techniques known in the art, for example monoclonal antibodies are produced by the techniques as described in Kohler F. & Milstein C., (1975), *Nature,* 256, 495–497.

In accordance with the present invention, the specific *H.pylori* HAP protein is useful in raising antibodies to the *H.pylori* HAP protein in experimental mammals and these specific anti-*H.pylori* HAP antibodies are useful in detecting the *H.pylori* HAP protein in clinical samples from a patient. The *H.pylori* HAP protein is also useful in ELISA or Western blot analysis, and can be purified from *H.pylori* organisms or produced by recombinant DNA technology, the procedures for which are all well recognised and well within the capabilities of the person skilled in the art.

Further provided by the present invention are hybridomas capable of producing monoclonal antibodies which recognize an antigenic determinant of *H.pylori* HAP protein, or a fragment thereof.

The present invention also provides a process for the amplification of a nucleic acid sequence as hereinbefore described by polymerase chain reaction (PCR) or equivalent technique known in the art such as transcription-aided amplification system (TAS). Preferably the PCR process is effected using the oligonucleotide pairs:

i) 5'- GCACAGGCAACAGGAACC- 3';
 and
 5'- AACGAGGCCTGAATTCTGC- 3'; or
ii) 5'- ATAACGTAGACCACCGGAGG- 3';
 and
 5'- TCCGGTGGTATTAACGAAGC- 3'

The present invention also provides nucleic acid probes comprising a nucleic acid sequence or part thereof as shown in FIG. 1. Also provided is a process for the identification of *H.pylori* nucleic acid comprising contacting a sample to be tested with a nucleic acid probe as hereinbefore described, under appropriate conditions known in the art, and detecting any hybridization of *H.pylori* nucleic acid sequence or sequences with the probe.

The selection of a particular probe, or pair of probes, will depend upon a number of factors, well understood in the art, and including amongst others the stringency requirements, i.e. the ability or otherwise of the probe to tolerate mismatching with the complementary sequence in the target DNA. Obviously the longer the probe the better the ability to withstand local mismatch without adversely affecting the hybridization of the probe to the target DNA. The factors affecting the choice of probe are well recognised and well within the capabilities of the person skilled in the art.

Also provided is a process for the identification of *H.pylori* nucleic acid comprising amplifying, in a sample to be tested, any *H.pylori* nucleic acid sequence as shown in FIG. 1 by PCR or equivalent technique and detecting the amplified nucleic acid sequences.

Although PCR amplification is the preferred method of *H.pylori* detection using *H.pylori* specific nucleotides of this invention, other detection procedures are available and are well known in the art. To this end the *H.pylori* specific oligonucleotides or nucleic acid probes of this invention may be provided with a variety of different labels such as radioactive, fluorescent or enzyme labels, all permitting the detection of any hybridized nucleotide bound to the unidentified nucleic acid sample under investigation.

Further provided is a method for the identification of *H.pylori* HAP protein antigenic determinants comprising contacting a sample to be tested with an antibody according to the present invention and detecting the presence of an antibody-antigen complex. Synonomously, there is also provided a method for the identification of *H.pylori* infection comprising contacting a sample to be tested with an *H.pylori* HAP protein or fragment thereof as hereinbefore described, or *V.cholerae* HAP protein or fragment thereof, and detecting the presence of an antigen-antibody complex. The sample to be tested will generally comprise dental plaque, saliva, gastric juices, or faeces or may comprise a sample of the gastric mucosa. As described above for the *H.pylori hap* nucleic acid sequences of the present invention the amino acid sequences, polypeptides, protein and antibodies may be provided with a variety of different labels such as fluoroescent, radioactive or enzymic labels, all permitting the detection of any amino acid sequence or antibody to the antibody or amino acid sequence sample under investigation, respectively.

*H.pylori* HAP antigens (the HAP protein or a fragment thereof) or *V.cholerae* HAP antigens, can be used in immunoassays to detect patients whom exhibit cross-reacting antibodies. Conversely antibodies can be used in immunoassays to detect patients whom exhibit cross-reacting *H.pylori* HAP antigens. Correlation can thus be made with *H.pylori* infection-associated gastroduodenal disease. The immunoassays contemplated by the present invention comprise diagnostic methods known in the art. The immunoassays may be based on direct antigen-antibody reactions, competition, single or double sandwich assays and include amplification systems such as those utilizing biotin and avidin.

The assays may comprise components attached to solid supports such as immunodiagnostic plates or glass beads or may involve immunoprecipitation. The immunoassays generally comprise use of a labelled antibody/antigen wherein the label may comprise fluorescent, chemiluminescent, radioactive or dye molecules.

Further, the present invention provides the use of the *H.pylori hap* nucleic acid, HAP amino acid, polypeptides, protein sequences and antibodies or *V.cholerae hap* nucleic acid or HAP protein or a fragment thereof for the manufacture of materials and kits for the diagnosis of gastric disorders associated with *H.pylori*. Accordingly kits are provided for by the present invention which comprise one or more of: a nucleic acid sequence encoding *H.pylori* HAP protein or a fragment thereof comprising all or part of the nucleic acid sequence of FIG. 1; *H.pylori* HAP protein or a fragment thereof comprising all or part of the amino acid sequence of FIG. 1; or *V.cholerae* HAP protein or a fragment thereof; or a polyclonal or monoclonal antibody which recognizes an antigenic determinant of the *H.pylori* HAP protein or a fragment thereof. There is also provided a kit for the identification of *H.pylori* using the polymerase chain reaction or equivalent technique comprising at least one of the pairs of oligonucleotides as hereinbefore described.

Kits according to the present invention may include appropriately labelled reagents, additional reagents and materials such as buffer solutions, means for detecting results of the assay and assay instructions. The kit components may be packaged in a suitable kit-container.

The present invention also provides the use of the following in the diagnosis of *H.pylori* infection: a nucleic acid sequence encoding *H.pylori* HAP protein or a fragment thereof comprising all or part of the nucleic acid sequence of FIG. 1; *H.pylori* HAP protein or a fragment thereof comprising all or part of the amino acid sequence of FIG. 1; or *V.cholerae* HAP protein or a fragment thereof; or a polyclonal or monoclonal antibody which recognizes an antigenic determinant of *H.pylori* HAP protein or a fragment thereof.

Thus, the use of the *H.pylori hap* nucleic acid sequence or fragment thereof or protein sequence or fragment thereof or antibodies directed against the *H.pylori* HAP protein covered by this invention include the manufacture of a kit or other materials for use in the diagnosis of gastric disorders associated with *H.pylori*. The *H.pylori hap* nucleic acid sequence or fragment thereof or protein sequences or fragment thereof or anti-*H.pylori* HAP antibodies may be combined with one or more other nucleic acid sequence or fragment thereof or protein sequence or fragment thereof or antibodies used in the diagnosis of gastric disorders associated with *H.pylori*.

The present invention is further described with reference to the following drawings in which:

FIG. 1 is a nucleotide sequence of the cloned 1.5 kb *H.pylori hap* gene fragment from *H.pylori* NCTC 11638 showing about 1 kb of coding sequence and about 500 bp of 3' flanking sequence. The sequence of this region of the *H.pylori hap* gene has been submitted to the EMBL Nucleotide Sequence Data Library under the accession number Z27239.

In FIG. 1. the numbering is from the first adenosine base (A) of the EcoRI site. The PCR primers are shown as dotted overlined arrows at positions 206–225 (HpHAP3), and 762–780 (HpHAP4). The three base in-frame deletion (marked Δ H) from the *V.cholerae hap* gene is at position 222, and the region identical to the *V.cholerae hap* gene extends from position 1 beyond the coding region (double underlined) except for a single addition at position 798 and a single deletion (of a T) at position 843. The stop codon is indicated by * * *.

Within the identified *H.pylori hap* nucleic acid sequence two regions have been identified as comprising coding regions for the active site component of the protein. The two regions are around nucleic acids numbered 16–18 (inclusive) encoding for tyrosine and 220–222 (inclusive) encoding for histidine. The region around nucleic acids numbered 43–45 (inclusive) encoding for glutamic acid has been identified as a putative zinc binding encoding region.

Within the sequence in FIG. 1 certain regions of the gene containing sequences have been identified that do not cross-hybridize with *Campylobacter* DNA. These include the nucleotides numbered as 1–174 (inclusive).

The present invention will now be described in more detail with reference to the following examples:

EXAMPLE 1

Growth of *H.pylori* Strains and Extraction of DNA and Proteins

*H.pylori* strains NCTC (National Collection of Type Cultures, London) 11637, 11638, 11916 and HP 34 (clinical isolate from a biopsy taken during endoscopy of a patient at Queen's Medical Centre, The University Hospital, Nottingham) were grown on Columbia blood agar with 5% horse blood (Oxoid) as a lawn for DNA extraction, for 2 days under microaerophilic conditions (Campypak, BBL) at 37° C. The resulting growth was harvested from four plates and was first Gram stained to identify the characteristic morphology. The cells were washed in 1 ml of lysis buffer (50 mM EDTA, 100 mM NaCl), and resuspended in 400 μl of lysis buffer to which 30 μl of lysis buffer containing 20% N-lauroylsarcosine (Sigma) was added. After five minutes incubation at room temperature, the suspension was repeatedly extracted with phenol saturated with TE (10 mM Tris-HCl, pH 8, 1 mM EDTA)buffer until no interface was evident. The nucleic acids were then ethanol precipitated overnight, collected by centrifugation, washed in 70% ethanol and the pellet air dried for 10 minutes. The DNA was then treated with proteinase K and purified using a Qiagen minicolumn according to the manufacturer's instructions. *H.pylori* strain NCTC 11638 was grown in liquid culture by adding one harvested plate of culture to 100 ml of Brucella broth (Difco) containing 2% β-cyclodextrin (Sigma) and 0.2 ml of reconstituted *H.pylori* selective supplement (Oxoid) in a 500 ml conical flask. The flask was incubated in an anaerobic jar with gentle shaking (100 r.p.m) for 3 days under microaerophilic conditions (Campypak, BBL) at 37° C. The *H.pylori* cells were collected by centrifugation and the proteins in the supernatant precipitated as previously described in Milton D. L., Norqvist, A., and Wolf Watz, H., (1992), *J. Bacteriol.*, 174,7235–7244. Cellular proteins were extracted by resuspending two plates of growth in 1.5 ml of protein-extraction buffer (10 mM Tris pH 7.5, 1 mM $MgCl_2$, 0.15 mM EDTA, 1 mM DTT, 1 mM PMSF, 2 $\mu gml^{-1}$ pepstatin A (Sigma) 0.5 $\mu gml^{-1}$ leupeptin (Sigma)), adding 200 $\mu l$ of 10% SDS and boiling for 5 minutes. The suspension was then cooled on ice for 5 minutes and the supernatant collected by centrifugation at 12500 r.p.m. for five minutes. The protein concentration was determined according to Bradford, M., (1976), *Anal Biochem*, 72,248–252, (Bio-Rad kit).

EXAMPLE 2

Identification of a *H.pylori* Protease Enzyme

40 $\mu$g of total cell and supernatant proteins from *H.pylori* NCTC 11638 and a clinical isolate of *P.aeruginosa* were separated on vertical minigels (Hoeffer Scientific), comprising a 5% acrylamide stacking gel and a 13% resolving gel, according to the procedure of Laemmli, UK., (1970), *Nature*, 227, 680–685. Electrophoresis was performed at 20 mA. Half of the gel was stained directly and the other half was incubated before staining to reveal protease activity. The gel portion that was stained directly was placed in a solution of 0.1% Coomassie brilliant blue R-250 in destain solution (40% methanol, 10% acetic acid, 50% water) for 1 h, and then placed in several changes of destain solution. The unstained gel was incubated, and the protease activity of this gel was detected by the procedures as described in Milton et al., 1992, *J.Bacteriol.*, 174,7235–7244, except that the gel was finally stained with Coomassie brilliant blue R-250 as above rather than amido black. Protease activity was identified in the gel by cleared bands (digestion of the gelatin and other proteins). Protease activity was clearly present in the *H.pylori* cell, supernatant and *P.aeruginosa* tracks. In the *H.pylori* tracks numerous proteolytic bands were present. An overloaded gel (100 $\mu$g of total *H.pylori* protein) run according to the above procedure showed a clear protease band at about 35 kDa.

The electrophoretic separation was transferred on to a nitrocellulose membrane by semi-dry blotting using transfer buffer (40 mM Tris pH8, 30 mM glycine, 20% methanol, 1.3 mM SDS) and an ATTO AE-6675 Horizblot transfer unit (Genetic Research International) according to the manufacturer's instructions. The nitrocellulose membrane was then dried and placed in blocking solution (1% bovine serum albumin in wash buffer (10 mM Tris pH 7.5, 100 mM NaCl,0.1% Tween 20)) for 1 hour at room temperature with constant rocking. The membrane was probed with either rabbit anti-*P.aeruginosa* elastase, Bever and Iglewski., 1988, *J. Bacteriol.*, 170:4309–4314, or pooled human sera absorbed with *E.coli* according to techniques well known in the art. The primary antibodies were added to the blocking buffer at 1:1000 and incubation was continued for 1 to 4 hours. The membrane was then briefly washed twice with wash buffer, once for 15 minutes and once for 5 minutes with rocking. The HRP-labelled antibody (either anti-rabbit or anti-human) was added to the membrane at a concentration of 1:1000 in wash buffer and incubated for 1 hour as above. The membrane was then washed once for 15 minutes, and four times for 5 minutes with wash buffer as above. The membrane was then developed using ECL substrate reagents (Amersham) and exposed to Fuji RX X-ray film and developed according to the manufacturer's instructions. Re-probing of blots was performed after stripping by incubating in 20 mM glycine pH 2.5, 0.055% Tween 20 overnight at room temperature with continuous shaking.

After probing with HRP labelled anti-rabbit antibodies, a strong band was visible in the *P.aeruginosa* track and a band of similar molecular weight to the *P.aeruginosa* elastase was seen in the *H.pylori* cellular protein extracts. After probing with the pooled sera from five patients with high-titre antibodies against *H.pylori*, a large number of bands were observed including a strong response to the band (35 kDa) previously identified by the anti-*P.aeruginosa* elastase antibody. After probing with pooled sera from five patients not infected with *H.pylori* no bands were visible. Thus, a protein of similar size and immuniological reactivity to the *P.aeruginosa* elastase protein was shown to be present in cellular and supernatant protein extracts of *H.pylori* NCTC 11638.

EXAMPLE 3

Cloning of the *H.pylori* hap Gene

5 $\mu$g of HindIII and BamHI digested *H.pylori* NCTC 11638 genomic DNA were separated and blotted onto Hybond N (Amersham) as described in Smith et al. (1992), *Gene*, 114:211–216. The genomic blots were probed overnight with 200 ng of a 3.2 kb HindIII fragment of *V.cholerae* hap gene DNA and 5 ng of HindIII—digested phage lambda DNA directly labelled with HRP (Amersham ECL kit), washed, developed and exposed to Fuji RX X-ray film according to the manufacturer's instructions. A 4 kb HindIII and a 1.5 kb BamHI fragment of *H.pylori* DNA hybridized strongly to the V.cholerae hap gene probe.

Figure 2:
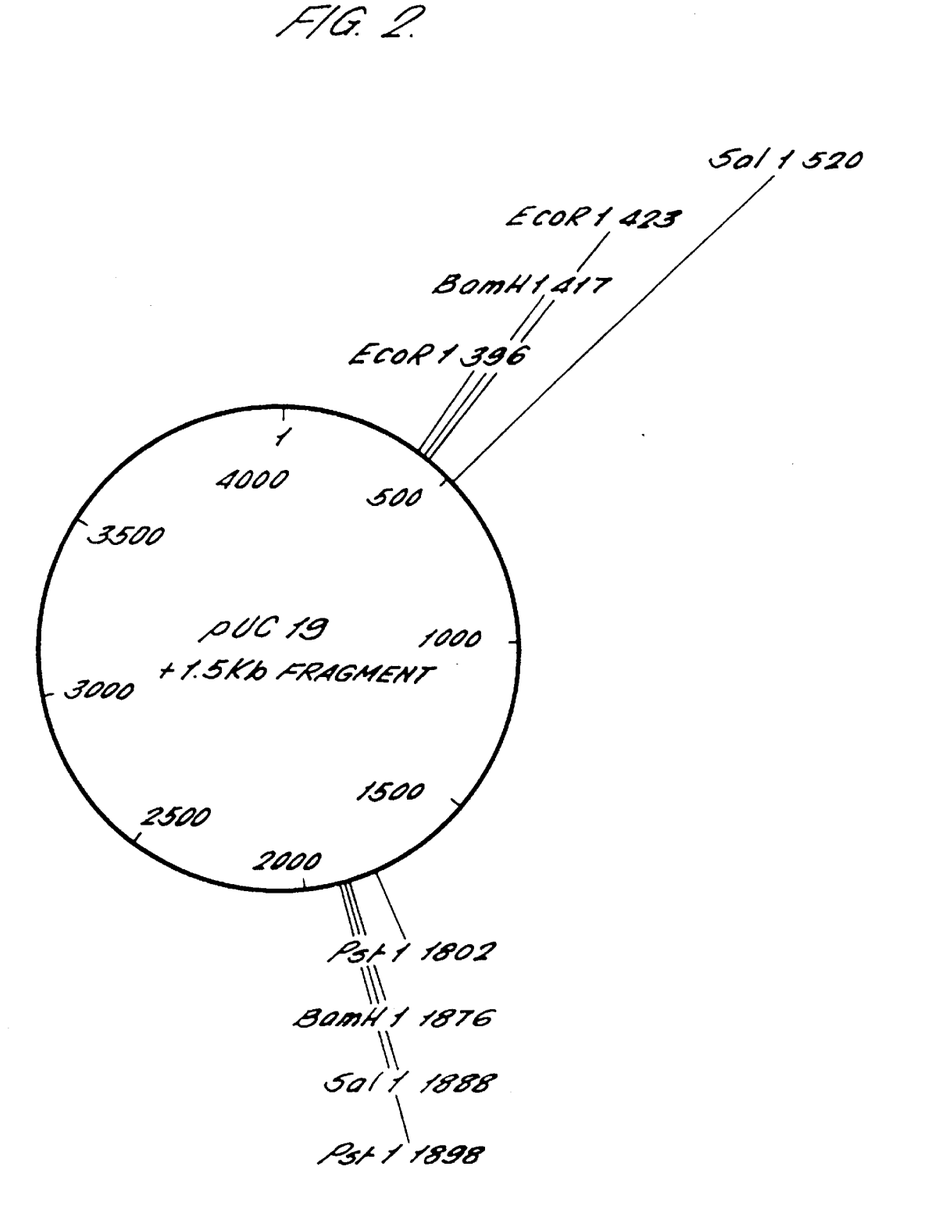
FIG. 2 is a map of the 1.5 kb fragment of the *H.pylori hap* gene in the plasmid pUC19. The *H.pylori hap* gene fragment is situated between the two BamHI sites.

Both the 4 kb (HindIII) and the 1.5 kb (BamHI) fragments were cloned from *H.pylori* NCTC 11638 genomic DNA by the following method:

Two 10 $\mu$g portions genomic DNA were digested with either BamHI or HindIII and size separated on a 0.5×TBE minigel. The 4 kb HindIII fragment and the 1.5 kb BamHI fragment were extracted from the gel and ligated separately into either HindIII or BamHI—digested (respectively) and calf alkaline phosphatased pUC18, pUC19 (FIG. 2) and pAT153 as described in Smith, A. W., (1990), Ph.D. Thesis, University of Nottingham, Nottingham, United Kingdom. The resultant plasmids were transformed into *E.coli* strain DH5α and plated out onto Lbroth agar plates containing 100 mg/l ampillicin and incubated overnight at 37° C. The desired recombinants were indentified by colony lifts onto Hybond N and screened by colony hybridization using the 3.2 kb HindIII *V.cholerae* (ECL) probe prepared above according to the manufacturer's instructions. The 1.5 kb BamHI fragment was sequenced in both directions using custom made, universal and reverse sequencing primers and Sequenase Version 2 (United States Biochemical Corporation) according to the manufacturer's instructions.

Sequencing of the 1.5 kb fragment did not reveal a start codon but did reveal a region of about 1 kb that was over 99% identical to the *V.cholerae* hap gene sequence with only three base in-frame deletion of a histidine residue in the coding region (ΔH in FIG. 1). The sequences diverge completely about 50 bp downstream of the stop codon, with the other bases differing before the complete divergence. The cloned sequence is then quite different from the 3'flanking region of the V.cholerae hap locus. Such coding sequence conservation is highly unusual and difficult to explain either by a common precursor gene or by intrageneric gene transfer. The %G+C content for H.pylori is 34–37% while for V.cholerae it is 46–48%, the subsequent difference in codon usage between the two genera should have allowed the DNA sequences to diverge even if the amino acid sequences were still conserved.

EXAMPLE 4

PCR of H.pylori Genomic DNA 50 ng of H.pylori genomic DNA from the four strains NCTC 11638, NCTC 11637, NCTC 11916 and HP34 were amplified using DynaZyme (Flowgen) thermastable polymerase according to the manufacturer's instructions. The primers used were either specific to the H.pylori hap gene 5'-GCACAGGCAACAGGAACC-3' and 5'-AACGAGGCCTGAATTCTGC-3' or those previously published to amplify a 411 bp fragment in the H.pylori ureA gene (Clayton et al, 1992 J.Clin.Microbiol 30,192–200 and Lopez et al, 1993, Mol.Cell Probes, 7,439–446.

The reaction cycle profiles were as follows, one cycle at 95° C. for 5 min; thirty cycles at 94° C. for 30 sec, either 52° C. (hap) or 48° C. (ureA) for 1 min, 72° C. for 1 min. 30 secs; and one cycle at 72° C. for 5 min. The PCR products were separated on 1.5% agarose Tris acetate gels, stained with ethidium bromide, blotted and hybridized as described in Example 2.

All four stains gave the 575 bp product predicted from the cloned hap gene sequence, although polymorphisms similar to those seen in the Southern blot analysis of strain HP34 were evident. Similarly, all four strains gave the 411 bp product from the ureA gene thereby confirming the origin of the genomic DNA. Genomic DNA from the nine Helicobacter species H.acinonyx, H.felis, H.fennelliae, H.canis, H.muridarum, H.nemestrinae, H.mustelae, H.cinaedi and H.pylori NCTC 11638 was amplified using the HAP gene primers and all nine gave a 575 bp fragment. Some polymorphisms were observed noticeably with H.acinonyx, H.felis, H-canis and H.nemestrinae, which were also evident from Southern analysis of genomic DNA from these species. This separation was blotted and probed with the V.cholerae hap gene and of the PCR products produced from H.pylori genomic DNA only the 575 bp hap fragment, and not the 411 bp (ureA) fragment, hybridized. The 575 bp PCR products from all nine Helicobacter species were shown to hybridize with the V.cholerae hap gene probe.

Due to the deletion between the H.pylori hap gene and the V.cholerae hap gene, PCR using non proof reading enzymes would result in no amplification of any homologous V.cholerae hap gene sequence present.

---

We claim:

1. An isolated nucleic acid molecule encoding *H. pylori* HAP protein comprising a nucleic acid molecule which encodes the amino acid sequence of Sequence I.D. No. 6.

2. The nucleic acid molecule as claimed in claim 1, comprising a nucleotide sequence (a) selected from the group consisting of nucleotides 1–936 of SEQ ID NO: 1 and 1–769 of SEQ ID NO: 1, and (b) complements of (a).

3. A nucleic acid molecule as claimed in claim 1 which is selected form the group consisting of genomic DNA, cDNA, and synthetic DNA.

4. A vector comprising a nucleic acid molecule as claimed in claim 3.

5. A vector as claimed in claim 4 which is pUC18 or pUC19.

6. A vector as claimed in claim 4 which is an expression vector.

7. A vector as claimed in claim 6 which is the expression vector pASK60-Strep.

8. A host cell transformed with a vector as claimed in claim 4.

9. A process for determining the expression of an *H. pylori hap* nucleic acid molecule comprising amplifying the *H. pylori hap* nucleic acid molecule using an oligonucleotide pair selected from the group consisting of (a) Sequence I.D. No. 2 and Sequence I.D. No. 3: and (b) Sequence I.D. No. 4 and Sequence I.D. No. 5.

10. A nucleic acid probe comprising a nucleic acid sequence comprising a nucleotide sequence selected from the group consisting of nucleotides 206–225, 762–180, 1–936 and 1–769 of SEQ ID NO:1, or a complementary sequence thereto.

11. A method for the identification of an *H. pylori* nucleic acid molecule comprising contacting a sample to be tested with a nucleic acid probe selected from the groups consisting of a probe comprising 15–50 contiguous nucleotides of Sequence I.D. No. 1 or its complement and a probe as claimed in claim 10, under appropriate conditions and detecting hybridization of the *H. pylori* nucleic acid molecule with the nucleic acid probe.

12. A method for the identification of *H. pylori* in a sample comprising amplifying an *H. pylori* nucleic acid molecule in the sample using an oligonucleotide pair selected from the group consisting of (a) Sequence I.D. No. 2 and Sequence I.D. No. 3; and (b) Sequence I.D. No. 4 and Sequence I.D. No. 5 and detecting the amplified nucleic acid molecule.

13. A kit for the identification of an *H. pylori* nucleic acid molecule comprising a nucleic acid molecule as claimed in claim 1.

14. A kit for the identification of *H. pylori hap* gene nucleic acid molecule by nucleic acid amplification comprising a pair of oligonucleotide primers comprising two non-overlapping contiguous fragments of SEQ ID NO: 1 or its complement.

15. A nucleic acid molecule encoding a fragment of *H. pylori* HAP protein comprising a nucleotide sequence selected from the group consisting of nucleotides 206–225, 762–780, 1–936, and 1–769 of Sequence I.D. No. 1.

16. An oligonucleotide of from 18–50 nucleotides of Sequence I.D. No. 1 selected from the group consisting of a nucleic acid molecule comprising the nucleotide sequence of Sequence I.D. No. 4 and a nucleic acid comprising the nucleotide sequence of Sequence I.D. No. 5.

17. A nucleic acid molecule comprising the nucleotide sequence of SEQ ID NO:1, wherein one of the codons encoding an amino acid is replaced with a stop codon.

18. A nucleic acid probe comprising a nucleic acid sequence comprising a nucleotide sequence of an oligonucleotide as claimed in claim 16.

* * * * *